United States Patent [19]

Yamatani et al.

[11] Patent Number: 4,508,912

[45] Date of Patent: Apr. 2, 1985

[54] PROCESS FOR PRODUCING N-CARBOBENZOXY-L-ASPARTIC ANHYDRIDE

[75] Inventors: Tetsuo Yamatani, Yokkaichi; Toyoto Hijiya, Yokosuka; Hideo Takeda, Inagi; Koji Shibuya, Ashiya; Kiichiro Tanaka, Tokyo, all of Japan

[73] Assignee: Ajinomoto Company, Incorporated, Tokyo, Japan

[21] Appl. No.: 479,898

[22] Filed: Mar. 29, 1983

[30] Foreign Application Priority Data

Mar. 30, 1982 [JP] Japan .................................. 57-51628
Mar. 30, 1982 [JP] Japan .................................. 57-51629

[51] Int. Cl.³ ............................................ C07D 307/66
[52] U.S. Cl. .................................................... 549/253
[58] Field of Search ........................................ 549/253

[56] References Cited

U.S. PATENT DOCUMENTS 4,332,718 6/1982 Takahasi et al. .................... 549/253

OTHER PUBLICATIONS

Tanaka et al., Chem. Abstracts vol. 80, (1974), 71101w.

Primary Examiner—Henry R. Jiles
Assistant Examiner—Bernard I. Dentz
Attorney, Agent, or Firm—Oblon, Fisher, Spivak, McClelland & Maier

[57] ABSTRACT

A process for producing a high yield of N-carbobenzoxy-L-aspartic anhydride from N-carbobenzoxy-L-aspartic acid in a very short period using commercially acceptable reaction conditions is disclosed. The process is characterized by reacting N-carbobenzoxy-L-aspartic acid with acetic anhydride in the presence of a metal oxide, a metal hydroxide, a metal salt of acid, an organobasic compound or an acid having a dissociation constant of $5 \times 10^{-2}$ or more.

11 Claims, No Drawings

4,508,912

PROCESS FOR PRODUCING N-CARBOBENZOXY-L-ASPARTIC ANHYDRIDE

FIELD OF THE INVENTION

The present invention relates to a process for producing N-carbobenzoxy-L-aspartic anhydride from N-carbobenzoxy-L-aspartic acid.

BACKGROUND OF THE INVENTION

The end compound of the present invention, i.e. N-carbobenzoxy-L-aspartic anhydride, is an important intermediate for peptide synthesis. For instance, this compound is reacted with a lower alkyl ester of L-phenylalanine, and by eliminating the protecting group (i.e. carbobenzoxy group) through hydrogenolysis, a lower alkyl ester of α-L-aspartyl-L-phenylalanine is produced. This peptide has the sweetness of sucrose and has a great potential for use as a new type of sweetener.

By dissolving or suspending N-carbobenzoxy-L-aspartic acid in a solvent and letting a dehydrating agent act on the resulting solution or suspension, N-carbobenzoxy-L-aspartic anhydride is produced as a solution or suspension. For commercial production, this solution or suspension is desirably reacted with a lower alkyl ester of L-phenylalanine without isolating the N-carbobenzoxy-L-aspartic anhydride, and for this reason, acetic anhydride which does not produce any by-product that may have adverse effects on the subsequent steps is preferably used as the dehydrating agent. The presence of a large amount of residual acetic anhydride in the reaction liquor should be avoided because this adversely affects the subsequent steps. Therefore, the proper amount of the acetic anhydride used as the dehydrating agent ranges from 0.7 to 1.3 mols per mol of the starting material N-carbobenzoxy-L-aspartic acid. To minimize the undesired conversion of the end product into a racemic form, the reaction temperature ranges from $-10°$ to $100°$ C., preferably from $0°$ to $80°$ C.

SUMMARY OF THE INVENTION

An object of the present invention is to provide a process for producing a high yield of N-carbobenzoxy-L-aspartic anhydride within a practically acceptable short reaction period using the above recommended amount of acetic anhydride and reaction temperature. This object of producing a high yield of the anhydride at an appreciably increased reaction rate can be achieved by adding a catalytic amount of oxides or hydroxides of various metals, salts of these metals with various acids, organobasic compounds or acids having a dissociation constant of $5\times10^{-2}$ or more.

DETAILED DESCRIPTION OF THE INVENTION

Metals that form oxides, hydroxides or acid salts include alkali metals such as lithium, sodium and potassium; alkaline earth metals such as magnesium and calcium; copper group elements such as copper; zinc group elements such as zinc; boron group elements such as aluminum; carbon group elements such as tin and lead; manganese group elements such as manganese; and iron group elements such as iron, cobalt and nickel. Illustrative acid salts are carbonates, carboxylic acid salts such as acetates, hydrochlorides, hydrobromides, nitrates, phosphates and sulfates. Effective organobasic compounds are triethylamine and tributylamine. Acids that can form salts with the above mentioned metals are those which have a dissociation constant of at least $5\times10^{-2}$, and examples are inorganic acids such as sulfuric acid, hydrochloric acid, hydrobromic acid, phosphoric acid, nitric acid and perchloric acid, and organic acids such as benzenesulfonic acid, toluenesulfonic acid, oxalic acid, trichloroacetic acid, trifluoroacetic acid and various carboxylic acids. Alkaline earth metal salts are particularly preferred.

The amount of these catalytic compounds used in the present invention differs slightly depending upon their type, but it should be held to a minimum level that does not adversely affect the subsequent steps. For example, as shown in Example 8 to be described later in this specification, magnesium acetate is added in a weight $8\times10^{-6}$ times as large as that of N-carbobenzoxy-L-aspartic acid (i.e. 8 ppm). As shown in Example 26, sulfuric acid is added in a weight $7\times10^{-3}$ times as large as that of N-carbobenzoxy-L-aspartic acid. The catalytic compounds listed above work effectively even if they are present in such small amounts.

When the process of the present invention is effected on an industrial scale, the proper amount of the above named catalytic compounds can be readily determined by those skilled in the art on the basis of preliminary experiments. The compounds are generally added at the time when the reaction for forming N-carbobenzoxy-L-aspartic anhydride is started, but an equally effective method is to prepare the starting material N-carbobenzoxy-L-aspartic acid in such a manner that the necessary amount of the catalytic compounds is deposited on the crystal of N-carbobenzoxy-L-aspartic acid. This can be accomplished by washing the isolated crystal of N-carbobenzoxy-L-aspartic acid with a dilute aqueous solution of any of the above listed compounds.

Any solvent that is inert to the reactants and the reaction product may be used in the process of the present invention. Typical solvents include ketones such as acetone and methyl ethyl ketone; ethers such as diethyl ether, tetrahydrofuran and dioxane; nitriles such as acetonitrile; esters such as ethyl acetate and methyl propionate; carboxylic acids such as formic acid, acetic acid and propionic acid; hydrocarbon halides such as chloroform, dichloromethane and ethylene dichloride; hydrocarbons such as toluene, xylene, hexane and cyclohexane; amides such as dimethylformamide; as well as dimethyl sulfoxide, γ-butyrolactone and nitromethane. These solvents may be used either alone or in mixture.

According to the process of the present invention, N-carbobenzoxy-L-aspartic anhydride from which an industrially very important lower alkyl ester of α-L-aspartyl-L-phenylanaline is derived can be produced in high yield and in a very short time.

The present invention is hereunder described in greater detail by reference to the following examples and comparative examples which are given here for illustrative purposes only and are by no means intended to limit the scope of the invention.

EXAMPLE 1

N-Carbobenzoxy-L-aspartic acid (80.2 g or 0.30 mol) was suspended in toluene (180 ml). While the suspension was held at $55°$ C. under stirring, 0.322 g ($1.5\times10^{-3}$ mol) of magnesium acetate tetrahydrate and 33.7 g (0.33 mol) of acetic anhydride were added, and the mixture was stirred at $55°$ C. for 3 hours. The resulting slurry was filtered under vacuum to produce 68.0 g of a crystal (isolation yield: 91%). The crystal had a melting point and IR absorption spectrum that agreed with those of a pure sample of N-carbobenzoxy-L-aspartic anhydride.

The same reaction was repeated and 10 ml of the resulting slurry was dissolved in a suitable amount of methanol including 5 vol% of triethylamine and toluene was removed from the solution under vacuum to obtain a concentrate which was dissolved in 50 ml of methanol. The solution was subjected to analysis by HPL chromatography on a column 635 A of Hitachi, Ltd. packed with Hitachi Gel #3011-0. Three predominant peaks appeared and they were found to correspond to N-carbobenzoxy-L-aspartic acid, α-methyl N-carbobenzoxy-L-aspartate, and β-methyl N-carbobenzoxy-L-aspartate by comparison with their respective pure samples. The production of methyl esters in both alpha and beta forms was due to the reaction between N-carbobenzoxy-L-aspartic anhydride and methanol. By determining the amounts of these esters, the content of N-carbobenzoxy-L-aspartic anhydride could be calculated. This method was used to determine the reaction yield for Example 1, which was found to be 100% on the 3rd hour of the reaction. The same method was used to calculate the reaction yield for Example 2 to 35 and Comparative Examples 1 to 4.

COMPARATIVE EXAMPLE 1

The procedure of Example 1 was repeated without adding magnesium acetate, and 10 ml of the resulting slurry was analyzed for the reaction yield, which was only 53.3%.

EXAMPLE 2 TO 21

The procedure of Example 1 was repeated using the reaction conditions listed in Table 1. The reaction yields for the respective examples are also shown in Table 1.

TABLE 1

| Example No. | Catalytic compound (g) | Solvent (ml) | Reaction yield (%) |
|---|---|---|---|
| 2 | NaOH ($6.0 \times 10^{-2}$) | Toluene (180) | 76.0 |
| 3 | $Na_2CO_3$ ($7.9 \times 10^{-2}$) | Toluene (180) | 76.4 |
| 4 | $Na.OCOCH_3$ ($1.2 \times 10^{-1}$) | Toluene (180) | 77.0 |
| 5 | $Li.OCOCH_3.2H_2O$ ($1.5 \times 10^{-1}$) | Toluene (180) | 92.4 |
| 6 | $K.OCOCH_3$ ($1.5 \times 10^{-1}$) | Toluene (180) | 63.8 |
| 7 | $Mg(OCOCH_3)_2.4H_2O$ ($3.2 \times 10^{-3}$) | Toluene (180) | 98.8 |
| 8 | $Mg(OCOCH_3)_2.4H_2O$ ($6.4 \times 10^{-4}$) | Toluene (180) | 94.8 |
| 9 | Basic manganese carbonate ($2.9 \times 10^{-2}$) | Toluene (180) | 99.0 |
| 10 | $MgCl_2.6H_2O$ ($3.0 \times 10^{-3}$) | Toluene (180) | 100 |
| 11 | $MgCl_2.6H_2O$ ($3.0 \times 10^{-3}$) | Ethyl acetate (180) | 98.5 |
| 12 | $MgCl_2.6H_2O$ ($3.0 \times 10^{-3}$) | Ethylene dichloride (180) | 99.0 |
| 13 | $Ca(OCOCH_3)_2.H_2O$ ($2.6 \times 10^{-1}$) | Toluene (180) | 100 |
| 14 | $Ca(OCOCH_3)_2.H_2O$ ($5.7 \times 10^{-1}$) | Toluene (180) | 81.6 |
| 15 | $Zn(OCOCH_3)_2.2H_2O$ ($3.3 \times 10^{-1}$) | Toluene (180) | 100 |
| 16 | $Al_2O(OCOCH_3)_4.4H_2O$ ($5.7 \times 10^{-1}$) | Toluene (180) | 56.7 |
| 17 | SnO ($2.0 \times 10^{-1}$) | Toluene (180) | 60.3 |
| 18 | $Pb(OCOCH_3)_2.3H_2O$ ($5.7 \times 10^{-1}$) | Toluene (180) | 72.0 |
| 19 | $Mn(OCOCH_3)_2.4H_2O$ ($3.7 \times 10^{-1}$) | Toluene (180) | 65.0 |
| 20 | $Fe(OH)_3$ ($1.6 \times 10^{-1}$) | Toluene (180) | 72.5 |
| 21 | Triethylamine ($1.5 \times 10^{-1}$) | Toluene (180) | 61.4 |

EXAMPLES 22 AND 23 AND COMPARATIVE EXAMPLE 2

The procedure of Example 1 was repeated using the reaction conditions shown in Table 2. The reaction yields for the respective cases are shown in the same table.

TABLE 2

| | Catalytic compound (g) | Reaction temp. (°C.) | Reaction yield (%) |
|---|---|---|---|
| Comparative Example 2 | none | 45 | 38.5 |
| Example 22 | $Mg(OCOCH_3)_24H_2O$ ($6.4 \times 10^{-4}$) | 45 | 70.3 |
| Example 23 | $Mg(OCOCH_3)_24H_2O$ ($6.4 \times 10^{-4}$) | 65 | 99.9 |

EXAMPLE 24

N-carbobenzoxy-L-aspartic acid (80.2 g or 0.30 mol) was suspended in toluene (180 ml). While the suspension was held at 55° C. under stirring, 0.15 g (0.0015 mol) of 98% sulfuric acid and 33.7 g (0.33 mol) of acetic anhydride were added, and the mixture was stirred at 55° C. for 3 hours. The resulting slurry was filtered under vacuum to produce 66.8 g of a crystal (isolation yield: 89%). The crystal had a melting point and IR absorption spectrum that agreed with those of a pure sample of N-carbobenzoxy-L-aspartic anhydride. The reaction yield for Example 24 was found to be 100% on the 3rd hour of the reaction.

COMPARATIVE EXAMPLE 3

The procedure of Example 24 was repeated without adding sulfuric acid, and 10 ml of the resulting slurry was analyzed for the reaction yield, which was only 53.3%.

EXAMPLES 25 TO 33

The procedure of Example 24 was repeated using the reaction conditions listed in Table 3. The reaction yields for the respective examples are shown in the same table.

TABLE 3

| Example No. | Catalytic comp. (g) | Solvent (ml) | Reaction yield (%) |
|---|---|---|---|
| 25 | Sulfuric acid (0.029) | Toluene (180) | 97.5 |
| 26 | Sulfuric acid (0.007) | Toluene (180) | 92.0 |
| 27 | Sulfuric acid (0.150) | Ethyl acetate (180) | 98.5 |
| 28 | Sulfuric acid (0.150) | Ethylene dichloride (180) | 98.0 |

TABLE 3-continued

| Example No. | Catalytic comp. (g) | Solvent (ml) | Reaction yield (%) |
|---|---|---|---|
| 29 | Phosphoric acid (0.147) | Toluene (180) | 100.0 |
| 30 | Nitric acid (0.095) | Toluene (180) | 62.5 |
| 31 | Toluenesulfonic acid (0.258) | Toluene (180) | 98.9 |
| 32 | Trichloroacetic acid (0.245) | Toluene (180) | 55.4 |
| 33 | Oxalic acid dihydrate (0.189) | Toluene (180) | 72.5 |

EXAMPLES 34 AND 35 AND COMPARATIVE EXAMPLE 4

The procedure of Example 24 was repeated using the reaction conditions shown in Table 4. The reaction yields for the respective experiments are shown in the same table.

TABLE 4

| | Catalytic comp. (g) | Reaction temp. (°C.) | Reaction yield (%) |
|---|---|---|---|
| Comparative Example 4 | None | 45 | 38.5 |
| Example 34 | $H_2SO_4$ (0.007) | 45 | 67.4 |
| Example 35 | $H_2SO_4$ (0.007) | 65 | 99.8 |

What is claimed is:

1. In a process for producing N-carbobenzoxy-L-aspartic acid anhydride which comprises reacting N-carbobenzoxy-L-aspartic acid with acetic anhydride, the improvement which consists of conducting the reaction in the presence of a catalytic amount of a metal oxide, a metal hydroxide, a metal salt of an acid, an organobasic compound or an acid having a dissociation constant of $5 \times 10^{-2}$ or more.

2. The process of claim 1 wherein the catalytic amount is no more than 0.011 moles of said metal oxide, metal hydroxide, metal salt of an acid, organobasic compound or acid having a dissociation constant of $5 \times 10^{-2}$ or more, per mole of N-carbobenzoxy-L-aspartic acid.

3. The process of claim 1 wherein the metal is selected from the group consisting of lithium, sodium, potassium, magnesium, calcium, copper, zinc, aluminum, tin, lead, manganese, iron, cobalt and nickel.

4. The process of claim 1 wherein the reaction is carried out in the presence of a metal oxide, a metal hydroxide or a metal salt of an acid wherein the metal portion is selected from the group consisting of lithium, sodium, potassium, magnesium, calcium, copper, zinc, aluminum, tin, lead, manganese, iron, cobalt and nickel.

5. The process of claim 1 wherein the metal salt of an acid is composed of a metal ion and an acid-derived cation which is selected from the group consisting of carbonate, acetate, chloride, bromide, nitrate, phosphate and sulfate.

6. The process of claim 1 wherein the reaction is carried out in the presence of a metal salt of an acid which is composed of a metal ion and an acid-derived cation selected from the group consisting of carbonate, acetate, chloride, bromide, nitrate, phosphate and sulfate.

7. The process of claim 1 wherein the organobasic compound is triethylamine or tributylamine.

8. The process of claim 1 wherein the reaction is carried out in the presence of an organobasic compound which is triethylamine or tributylamine.

9. The process of claim 1 wherein the acid having a dissociation constant of $5 \times 10^{-2}$ or more is selected from the group consisting of toluenesulfonic acid, oxalic acid, trichloroacetic acid, sulfuric acid, phosphoric acid and nitric acid.

10. The process of claim 1 wherein the metal oxide, metal hydroxide or a metal salt of an acid is selected from the group consisting of NaOH, $Na_2CO_3$, Na(OCOCH$_3$), Li(OCOCH$_3$), K(OCOCH$_3$), Mg(OCOCH$_3$)$_2$, basic manganese carbonate, MgCl$_2$, Ca(OCOCH$_3$)$_2$, Zn(OCOCH$_3$)$_2$, Al$_2$O(OCOCH$_3$)$_4$, SnO, Pb(OCOCH$_3$)$_2$, Mn(OCOCH$_3$)$_2$, and Fe(OH)$_3$.

11. The process of claim 1 wherein the reaction is carried out in the presence of a metal oxide, metal hydroxide or a metal salt of an acid which is selected from the group consisting of NaOH, $Na_2CO_3$, Na(OCOCH$_3$), Li(OCOCH$_3$), K(OCOCH$_3$), Mg(OCOCH$_3$)$_2$, basic manganese carbonate, MgCl$_2$, Ca(OCOCH$_3$)$_2$, Zn(OCOCH$_3$)$_2$, Al$_2$O(OCOCH$_3$)$_4$, SnO, Pb(OCOCH$_3$)$_2$, Mn(OCOCH$_3$)$_2$, and Fe(OH)$_3$.

* * * * *